United States Patent
Someya et al.

(10) Patent No.: US 11,291,114 B2
(45) Date of Patent: Mar. 29, 2022

(54) ELECTRONIC FUNCTIONAL MEMBER AND ELECTRONIC COMPONENT

(71) Applicant: JAPAN SCIENCE AND TECHNOLOGY AGENCY, Saitama (JP)

(72) Inventors: Takao Someya, Tokyo (JP); Sunghoon Lee, Tokyo (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 42 days.

(21) Appl. No.: 16/980,496

(22) PCT Filed: Mar. 13, 2019

(86) PCT No.: PCT/JP2019/010292
§ 371 (c)(1),
(2) Date: Oct. 8, 2020

(87) PCT Pub. No.: WO2019/177030
PCT Pub. Date: Sep. 19, 2019

(65) Prior Publication Data
US 2021/0029824 A1 Jan. 28, 2021

(30) Foreign Application Priority Data
Mar. 15, 2018 (JP) .............................. JP2018-048388

(51) Int. Cl.
*H05K 1/16* (2006.01)
*H05K 1/03* (2006.01)
*A61B 5/25* (2021.01)

(52) U.S. Cl.
CPC ............. *H05K 1/0393* (2013.01); *A61B 5/25* (2021.01); *H05K 1/16* (2013.01); *A61B 2562/164* (2013.01); *H05K 2201/10151* (2013.01)

(58) Field of Classification Search
CPC ....................... H05K 1/16–167; H05K 1/0393
See application file for complete search history.

(56) References Cited

U.S. PATENT DOCUMENTS

| | | | |
|---|---|---|---|
| 6,080,690 | A | 6/2000 | Lebby et al. |
| 2006/0003090 | A1 | 1/2006 | Rodger et al. |
| 2016/0100768 | A1 | 4/2016 | Someya et al. |

FOREIGN PATENT DOCUMENTS

| | | |
|---|---|---|
| EP | 3468313 A1 | 10/2019 |
| JP | 2016112246 A | 6/2016 |
| JP | 6168507 B | 7/2017 |

(Continued)

OTHER PUBLICATIONS

Japan Patent Office, "International Search Report for PCT Application No. PCT/JP2019/010292", Japan, dated Jun. 4, 2019.

(Continued)

*Primary Examiner* — Jeremy C Norris
(74) *Attorney, Agent, or Firm* — Tim Tingkang Xia, Esq.; Locke Lord LLP (57) ABSTRACT

This fiber net includes a fiber net having an electrode part, in which a fiber constituting the electrode part includes a core material, a relaxation layer which covers at least a part of a surface of the core material and contains a material having a higher Young's modulus than a material forming the core material, and a conductive layer which covers a surface of the relaxation layer on a side opposite to the core material side.

15 Claims, 5 Drawing Sheets

(56) References Cited

FOREIGN PATENT DOCUMENTS

| JP | 2017208492 A | 11/2017 |
|---|---|---|
| WO | 2017140768 A1 | 8/2017 |
| WO | 2017203685 A1 | 11/2017 |

OTHER PUBLICATIONS

Tian, Bozhi et al., "Macroporous nanowire nanoelectronic scaffolds for synthetic tissues", Nature Materials, Nov. 2012, vol. 11, pp. 986-994.

Feiner, Ron et al., "Engineered hybrid cardiac patches with multi-functional electronics for online monitoring and regulation of tissue function", Nat mater., Jun. 2016; 15(6), pp. 679-685.

Office Action Issued by the Japan Patent Office for Application No. 2018-048388, dated Aug. 24, 2021, Japan.

Search Report Issued by the European Patent Office dated Nov. 16, 2021 for European Patent Application No. 19768243.8.

ELECTRONIC FUNCTIONAL MEMBER AND ELECTRONIC COMPONENT

CROSS-REFERENCE TO RELATED PATENT APPLICATION

This application claims priority to Japanese Patent Application No. 2018-048388 filed in Japan on Mar. 15, 2018, the whole content of which is incorporated herein by reference.

TECHNICAL FIELD

The present invention relates to an electronic functional member and an electronic component.

BACKGROUND OF THE INVENTION

In recent years, flexible electronics have come to have various applications due to the softness of the materials thereof and have attracted much attention. Above all, interest in the healthcare field has increased with the aging of society worldwide. For example, flexible electronics have attracted attention as a means for obtaining biological information directly from cells and tissues by being mounting on a surface of the human body or inside the body.

Generally, flexible electronics are fabricated by forming electronic devices on a flexible base material, but it cannot be said that the flexibility thereof is sufficient. Therefore, it cannot be said that surface conformability is sufficient, and highly accurate information may not be able to be obtained or discomfort during mounting may not be able to be reduced sufficiently.

In order to solve such problems, the present inventors have developed an electronic functional member using a fiber net made of a resin composition (Patent Document 1 and Patent Document 2).

CITATION LIST

Patent Document 1: Japanese Unexamined Patent Application, First Publication No. 2016-112246
Patent Document 2: PCT International Publication No. WO 2017/203685

SUMMARY OF THE INVENTION

Technical Problem

The electronic functional members described in Patent Document 1 and Patent Document 2 have excellent flexibility and a property of being extendable and contractible due to voids provided in the fiber net. On the other hand, when measurement is attempted on a very soft material (Young's modulus of several kPa) which is in motion, such as, for example, cardiomyocytes, there are cases in which a part of a conductive layer patterned on the fiber net becomes damaged.

The present invention has been made in view of the above circumstances, and an objective of the present invention is to provide an electronic functional member and an electronic component in which damage to a conductive layer at the time of being extended and contracted can be curbed.

Solution to Problem

As a result of intensive research, the present inventors have found that, damage to a conductive layer can be prevented by forming an electrode part, which is a measurement point, into a three-layer structure including a core material, a relaxation layer, and a conductive layer.

That is, in order to solve the above-described problems, the following means were employed.

(1) An electronic functional member according to a first aspect includes a fiber net which includes an electrode part, in which a fiber which constitutes the electrode part includes a core material, a relaxation layer which covers at least a part of a surface of the core material and contains a material which has a higher Young's modulus than a material which forms the core material, and a conductive layer which covers a surface of the relaxation layer on a side opposite to the core material side.

(2) In the electronic functional member according to the above-described aspect, a Young's modulus of the material which forms the core material may be lower than 1 GPa, and a Young's modulus of a material which forms the relaxation layer may be 1 GPa or higher.

(3) In the electronic functional member according to the above-described aspect, the material which forms the core material may be polyurethane or silicon rubber, and a material which forms the relaxation layer may be parylene.

(4) In the electronic functional member according to the above-described aspect, the conductive layer may be made of gold or platinum.

(5) In the electronic functional member according to the above-described aspect, the diameter of the core material may be 200 nm or more and 2000 nm or less, and the thickness of the relaxation layer may be 50 nm or more and 500 nm or less.

(6) The electronic functional member according to the above-described aspect may further include a wiring part which continuously extends from the electrode part, in which a fiber which constitutes the wiring part may include the core material, the relaxation layer, the conductive layer, and a cover layer which covers a surface of the conductive layer on a side opposite to the relaxation layer side.

(7) In the electronic functional member according to the above-described aspect, a fiber which constitutes a portion of the fiber net excluding the electrode part and the wiring part may be formed of a core material.

The core material of the electrode part, the core material of the wiring part, and the core material included at a portion other than these parts may be formed of the same material. The core material, the relaxation layer, and the conductive layer may be formed of the same materials as for the electrode part and the wiring part.

(8) An electronic component according to a second aspect includes the electronic functional member according to the above-described aspect, and an electronic circuit element connected to the wiring part of the electronic functional member.

Advantageous Effects of the Invention

According to the electronic functional member of one aspect of the present invention, damage to the conductive layer at the time of being extended and contracted can be curbed.

According to the electronic component of one aspect of the present invention, it is possible to conform to and measure an object that has a softness in the order of kPa and is in motion.

DESCRIPTION OF EMBODIMENTS

Hereinafter, a configuration of the present embodiment will be described with reference to the drawings. In the drawings used in the following description, featured parts may be illustrated in an enlarged manner so that the features can be better understood, and dimensional ratios and the like between respective constituent elements may not be the same as the actual ones. Materials, dimensions, and the like illustrated in the following description are merely examples, and the present embodiment is not limited thereto and can be implemented with appropriate modifications within a range not changing the gist thereof. Unless otherwise specified, members, numbers, amounts, materials, shapes, positions, types, ratios, methods, steps, or the like may be changed, added, and/or omitted as needed.

Electronic Functional Member

Figure 1:
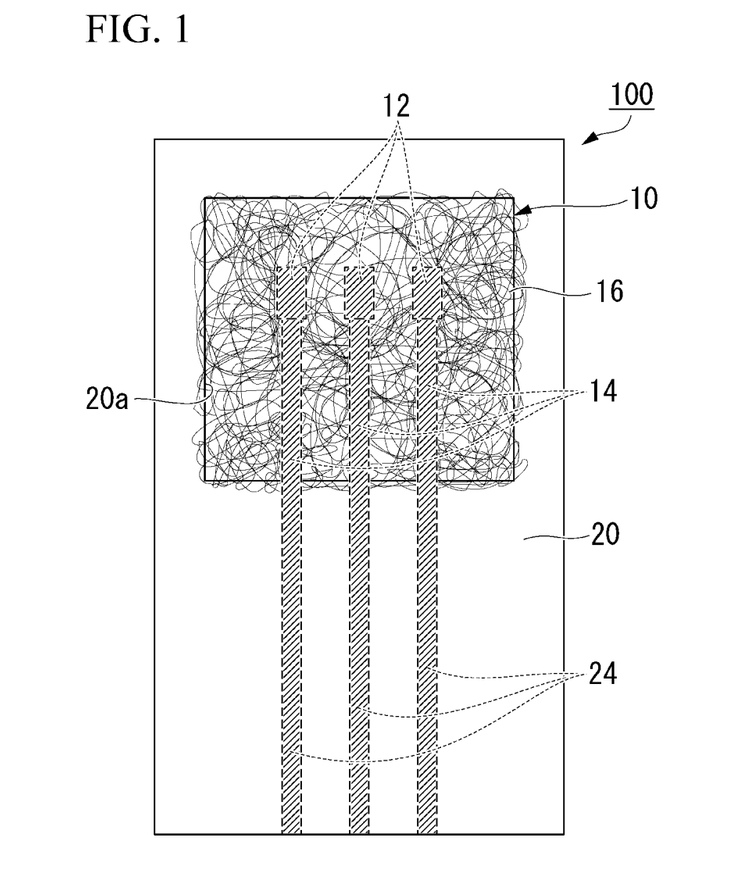
FIG. 1 is a schematic view illustrating a preferred example of an electronic functional member according to a first embodiment.

FIG. 1 is a schematic plan view of an electronic functional member according to the present embodiment. An electronic functional member 100 illustrated in FIG. 1 includes a fiber net 10 and a base material 20 that supports the fiber net 10. The base material 20 preferably has an opening 20a. The fiber net 10 is suspended in the opening 20a of the base material 20. In order to realize a state of being "suspended in the opening," the fiber net 10 is fixed to one surface of the base material 20 across the opening 20a of the base material 20. That is, the fiber net 10 is disposed on the base material 20 to cover the opening 20a. The electronic functional member can be used as, for example, a member (sensor) that receives information from a living body by bringing it into contact with the living body, a member or an electrode that gives an electrical signal to a living body, or the like.

Fiber Net

The fiber net 10 is an aggregate of fibers. In FIG. 1, a fiber (core material) constituting the fiber net 10 is illustrated as lines for facilitating understanding. The fiber net 10 may have an arbitrarily selected shape and/or configuration. The fiber constituting the fiber net 10 may connect between the opening 20a, for example, in a linear shape such as vertically, horizontally, diagonally, or any combination thereof, or in a curved shape such as a random shape, a repeating shape, or a wave shape. A linear shape and a curved shape may be used in combination. Also, the fiber may be suspended on the opening 20a by an outer frame in a stretched state due to a tension or in a bent state. For example, the fiber net 10 may be formed in a cotton form or a felt form. The fiber may consist of only one or more continuous fibers and/or formed of a plurality of fibers that are not continuous with each other. A combination of these may also be used. The fiber net may also have a three-dimensional network shape. The number of fibers in the fiber net can be arbitrarily selected. For example, the number of fibers may be 1 to 500, 500 to 2000, or 2000 to tens of thousands, or may be a number greater than these.

Although a total thickness of the fiber net 10 can be arbitrarily selected, it is preferably 200 nm or more and 100 µm or less, and more preferably 500 nm or more and 80 µm or less. Here, "total thickness of the fiber net 10" means a thickness from one surface of the fiber net to another surface thereof. The total thickness of the fiber net 10 can be measured as a gap dimension, for example, when it is sandwiched by flat plates. Further, it is difficult to measure and define those described above when a fiber density is very sparse, but it is not necessary to consider the case in which a fiber density is very sparse because sufficient conductivity cannot be secured in this case. When the total thickness of the fiber net 10 is 200 nm or more, the fiber net 10 has a sufficient strength. On the other hand, when the total thickness of the fiber net 10 is 100 µm or less, a resistance between surfaces to be measured can be sufficiently ignored.

The fiber net 10 includes an electrode part 12, a wiring part 14, and a support part 16. The electrode part 12, the wiring part 14, and the support part 16 are all aggregates of fibers. The electrode part 12, the wiring part 14, and the support part 16 are formed of fibers and voids between the fibers. Structures of fibers constituting the electrode part 12, the wiring part 14, and the support part 16 are different from each other. However, they preferably have a core material of the same type.

Forms of the electrode part 12 and the wiring part 14 are not particularly limited and can be changed as needed.

For example, in a case of obtaining information on a living body, the electrode part 12 can be patterned according to a region of the living body. An electric signal from each contact region can be obtained, when the patterned electrode part 12 is brought into contact with the region of the living body.

Electrode Part

Figure 2:
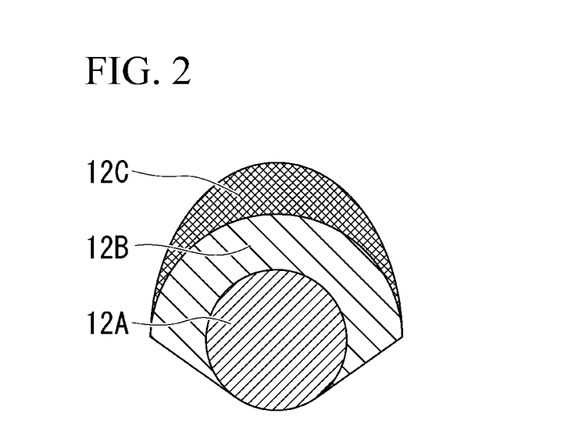
FIG. 2 is a view schematically illustrating a preferred example of a cross section of a fiber constituting an electrode part according to the first embodiment.

FIG. 2 is a view schematically illustrating an example of a cross section of a fiber constituting the electrode part 12 according to a first embodiment. As illustrated in FIG. 2, the fiber constituting the electrode part 12 includes a core material 12A, a relaxation layer 12B, and a conductive layer 12C. In the present example, when viewed from the cross section of FIG. 2, a structure is shown such that the conductive layer 12C is formed only on an upper side, and a lower side of the relaxation layer 12B has been removed after formation of the layer. The present invention is not limited only to the present example. Further, the fiber constituting the electrode part may be a plurality of fibers, and the electrode part may have a portion in which the fibers are in contact with each other.

The core material 12A is a part which is provided as core of the fiber that constitutes the electrode part 12. Although a Young's modulus of a material forming the core material 12A can be arbitrarily selected, it is preferably lower than 1 GPa, more preferably 100 MPa or lower, and still more preferably 10 MPa or lower. The lower limit value of the Young's modulus can be arbitrarily selected. When the core material 12A is extremely soft and extendable and contractible, the core material 12A conforms to an object to be measured without limiting movement of the object to be measured that is soft and in motion.

Here, "Young's modulus of a material forming the core material 12A" is not a Young's modulus of the fiber constituting the core material 12A, but means a Young's modulus of a material measured by the method in accordance with JIS 7161 using the material forming the core material 12A.

The material forming the core material 12A can be arbitrarily selected, and for example, a generally used elastomer such as a fluorine-based rubber, urethane-based rubber, or silicone-based rubber, a polymer material other than an elastomer such as acryl, nylon, or polyester, polyvinyl alcohol (PVA), polyvinyl pyrrolidine (PVP), polyglycolic acid (PGA), polylactic acid (PLA), or the like can be used alone or in combination of two or more types.

Polyurethane, which is a type of urethane-based rubber, and silicone rubber, which is a type of silicone-based rubber, have an excellent property of being extendable and contractible and can conform to movement of an object which is a very soft material (Young's modulus of several kPa) and in motion such as, for example, cardiomyocytes. It is also possible to avoid limiting movement of the object.

Although a diameter of the core material 12A can be arbitrarily selected, it is preferably 200 nm or more and 2000 nm or less, more preferably 300 nm or more and 1500 nm or less, still more preferably 500 nm or more and 1000 nm or less, and particularly preferably 700 nm or less and 800 nm or less. When the diameter of the core material 12A is within the above range, a property of being extendable and contractible and flexibility of the core material 12A can be secured. Although the cross section of the core material 12A is circular, a shape other than that may also be used. The same diameter may be maintained continuously along the core material 12A, or the diameter may change midway therealong.

The diameter of the core material 12A can be obtained as an average value of diameters by measuring cross sections of the resin composition at arbitrary 10 points with a scanning electron microscope.

Figure 3:
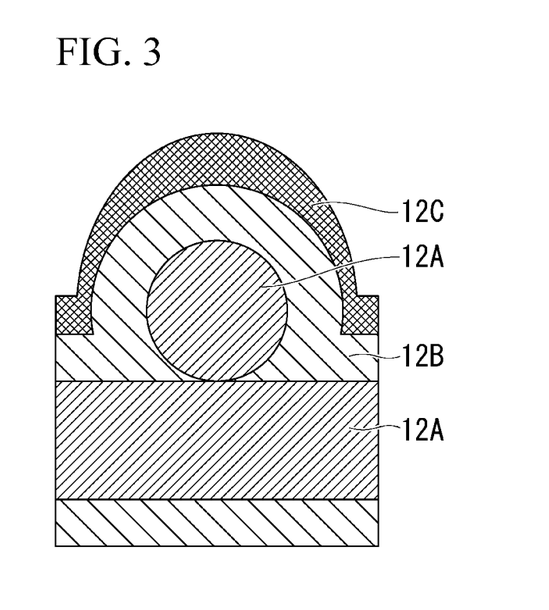
FIG. 3 is a view schematically illustrating a preferred example of a cross section of an intersection point of the fibers constituting the electrode part according to the first embodiment.

FIG. 3 is a view schematically illustrating a cross section of an intersection point of the fibers constituting the electrode part 12 according to the first embodiment. The intersection point illustrated in FIG. 3 is an intersection point of the core material 12A extending from the left to the right in the illustration and the core material 12A extending from in front of to behind the paper surface. At the intersection point, the core materials 12A are preferably partially bound to each other. When the core materials 12A are bound to each other, the strength of the fiber net can be increased.

The relaxation layer 12B covers at least a part of a surface of the core material 12A. That is, the relaxation layer 12B may cover all or a part of the surface of the core material. The relaxation layer 12B contains a material having a higher Young's modulus than the material forming the core material 12A. A Young's modulus of the material forming the relaxation layer 12B is higher than a Young's modulus of the material forming the core material 12A and lower than a Young's modulus of the material forming the conductive layer 12C. Here, "Young's modulus of the material forming the relaxation layer 12B" is not a Young's modulus of the fiber constituting the relaxation layer 12B, but means a Young's modulus of a material measured by the method in accordance with JIS 7161 wherein the material forming the relaxation layer 12B is used.

The relaxation layer 12B alleviates a stress applied to the conductive layer 12C due to a difference in a property of being extendable and contractible and flexibility between the core material 12A and the conductive layer 12C which is to be described below, and suppresses breakage of the conductive layer 12C. When the relaxation layer 12B prevents the conductive layer 12C from breaking, the electronic functional member 100 can be used for measuring a softer object. It is surprising that, for measuring a soft object, damage to the conductive layer 12C can be prevented by providing the relaxation layer 12B that is harder than the core material 12A between the core material 12A and the conductive layer 12C.

Although the Young's modulus of the material forming the relaxation layer 12B can be arbitrarily selected, it is preferably 500 MPa or higher, and more preferably 1 GPa or higher. Also, the Young's modulus of the material forming the relaxation layer 12B is preferably 50 GPa or lower, and more preferably 10 GPa or lower. When the Young's modulus of the relaxation layer 12B is within the above range, a stress applied to the conductive layer 12C due to a difference in a property of being extendable and contractible and flexibility between the core material 12A and the conductive layer 12C can be further alleviated.

Although the material forming the relaxation layer 12B can be arbitrarily selected, for example, parylene, polyimide, polyethylene terephthalate (PET), polyethylene naphthalate (PEN), epoxy resins (for example, photosensitive resist (SU8): manufactured by Nippon Kayaku Co., Ltd), or the like can be used. Parylene can be coated in a thin film and has excellent biocompatibility.

Although a thickness of the relaxation layer 12B can be arbitrarily selected, it is preferably ⅛ or more and ½ or less of the diameter of the core material 12A, more preferably ⅙ or more and ⅓ or less of the diameter, and still more preferably ¼ of the diameter. Specifically, the thickness of the relaxation layer 12B is preferably 50 nm or more and 500 nm or less, more preferably 80 nm or more and 400 nm or less, still more preferably 100 nm or more and 300 nm or less, and particularly preferably 150 nm more and 250 nm or less.

The thickness of the relaxation layer 12B can be obtained as an average value of diameters by measuring cross sections of the resin composition at arbitrary 10 points with a scanning electron microscope. The relaxation layer 12B can be partially removed by etching or the like to be described below. When the thickness of the relaxation layer 12B is not uniform due to the removal, the thickness of a thickest portion may be measured.

Also, the relaxation layer 12B has an excellent step coverage property with respect to the core material 12A and also plays a role of supporting the core material 12A. "Excellent step coverage property" may also mean excellent step-difference coverage. The core material 12A is very soft, and it is difficult to maintain its shape alone. When the relaxation layer 12B alleviates a stress difference between the core material 12A and the conductive layer 12C while partially supporting the soft core material 12A, it is possible to conform to an object without hindering movement of the object in motion. Such a configuration is particularly useful when the core material 12A does not have solubility (biological solubility).

Figure 4:
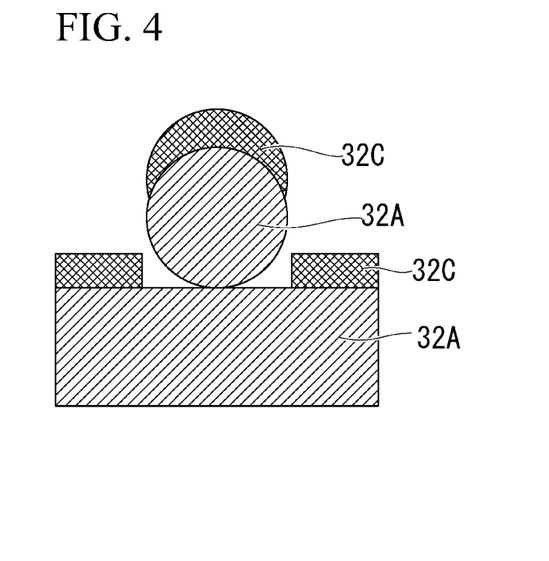
FIG. 4 is a view, for comparison, schematically illustrating an example in which one surface of an intersection point of core materials on which a relaxation layer is not formed is covered with a conductive layer.

Also, since the relaxation layer 12B has an excellent step coverage property, the relaxation layer 12B can cover the intersection point of the core materials 12A and 12A as illustrated in FIG. 3. When the core materials 12A are covered with the relaxation layer 12B, continuity of the conductive layer 12C formed on one surface thereof is enhanced. Also, when the relaxation layer 12B supports the core material 12A, disconnection of the conductive layer 12C during measurement of an object in motion is prevented. For comparison, FIG. 4 is a view schematically illustrating an example in which one surface of an intersection point of core materials 32A on which a relaxation layer is not formed is covered with a conductive layer 32C. As illustrated in FIG. 4, when there is no relaxation layer, the conductive layer 32C is not formed in a portion which is located in a shadow of the core material 32A, and continuity of the conductive layer 32C deteriorates.

As illustrated in FIG. 2, in the present embodiment, the conductive layer 12C covers a surface of the relaxation layer 12B on a side opposite to the core material 12A side. The conductive layer 12C can cover at least a part or all of the surface of the relaxation layer 12B excluding a portion in contact with the core material 12A. The conductive layer 12C is made of a material having conductivity. The material can be arbitrarily selected. For example, a metal such as copper, gold, aluminum, silver, or zinc, or an organic conductive material which is exemplified by PEDOT/PSS can be preferably used. One type of these or two or more types in combination may be used. Among them, copper or silver is preferable from a viewpoint of conductivity. Also, when it is used in a living body or the like, it is preferable to use stable gold or platinum in order to suppress unnecessary reactions.

A thickness of the conductive layer 12C can be arbitrarily selected and is preferably 20 nm to 2000 nm, more preferably 20 nm to 1000 nm, and still more preferably 50 nm to 100 nm. Within these ranges, sufficient conductivity and flexibility can be obtained. The thickness of the conductive layer 12C can be measured by the same method as that in the diameter of the core material 12A of the fiber net. When the thickness of the conductive layer 12C is not uniform, a thickness of a thickest portion may be measured. A cross-sectional shape of the conductive layer 12 can be arbitrarily selected, and for example, the cross-sectional shape may be an approximate crescent moon or may include a part of an approximate crescent-shape. In the example illustrated in the drawing, the conductive layer 12C is not in contact with the core material 12A. A Young's modulus of the material forming the conductive layer 12C can be arbitrarily selected. The conductive layer 12C may be exposed in the air.

Wiring Part

The wiring part 14 extends from the electrode part 12. The wiring part 14 of the fiber net 10 is connected to a wiring part 24 of the base material 20. In the present embodiment, the wiring part 14 of the fiber net 10 and the wiring part 24 of the base material 20 are simultaneously patterned and are continuously connected. A fiber included in the wiring part 14 may also be a plurality of fibers and may have a portion in which the fibers are in contact with each other. Further, the wiring part 24 includes a relaxation layer, a conductive layer, and a cover layer, but may or may not include a core material.

Figure 5:
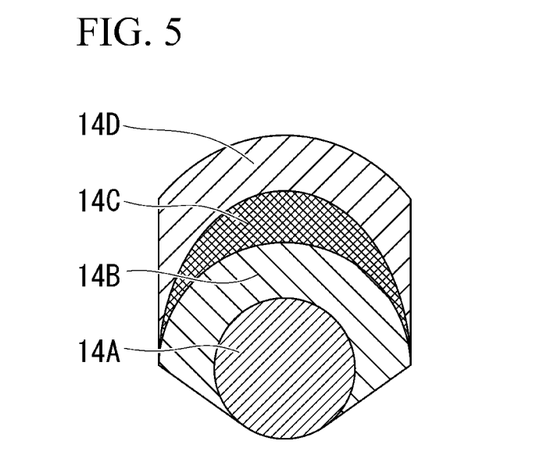
FIG. 5 is a view schematically illustrating a preferred example of a cross section of a fiber constituting a wiring part according to the first embodiment.

FIG. 5 is a view schematically illustrating a cross section of a fiber constituting the wiring part 14 according to the first embodiment. As illustrated in FIG. 5, the fiber constituting the wiring part 14 includes a core material 14A, a relaxation layer 14B, a conductive layer 14C, and a cover layer 14D. The core material 14A, the relaxation layer 14B, and the conductive layer 14C are the same as the core material 12A, the relaxation layer 12B, and the conductive layer 12C in the electrode part 12.

The cover layer 14D covers a surface of the conductive layer 14C on a side opposite to the relaxation layer 14B side. The cover layer 14D can cover at least a part or all of the surface of the conductive layer 14C excluding a portion in contact with the relaxation layer 14B. It is preferable to cover all the surface. The cover layer 14D can prevent short-circuiting between the conductive layer 14C and an object to be measured. Also, the wiring part 14 is configured to include the cover layer 14D, and the electrode part 12 is configured not to include the cover layer 14D, whereby an electric potential measurement position can be easily determined. For example, when cells or the like are measured, it is required to clarify which portion will be measured. When the electric potential measurement position is clarified, it is even possible to clarify which portion of the cells or the like will be measured.

The cover layer 14D can be formed of any material, and the same material as that of the relaxation layer 14B can be preferably used. A thickness of the cover layer 14D can be arbitrarily selected and is preferably 50 nm or more and 500 nm or less, more preferably 80 nm or more and 400 nm or less, still more preferably 100 nm or more and 300 nm or less, and particularly preferably 150 nm or more and 250 nm or less. The thickness of the cover layer 14D can be obtained as an average value of diameters by measuring cross sections of the resin composition at arbitrary 10 points with a scanning electron microscope. When the thickness of the cover layer 14D is not uniform, the thickness of a thickest portion can be measured.

Support Part

Figure 6:
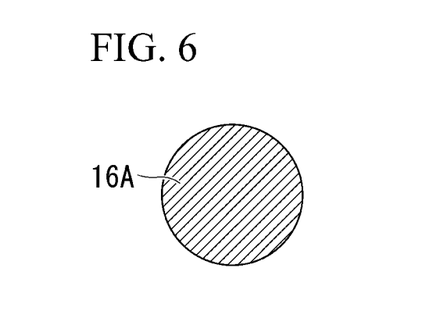
FIG. 6 is a view schematically illustrating a preferred example of a cross section of a fiber constituting a portion other than the electrode part and the wiring part according to the first embodiment.

The support part 16 is a portion of the fiber net 10 excluding the electrode part 12 and the wiring part 14. FIG. 6 is a view schematically illustrating a cross section of a fiber constituting the support part 16 according to the first embodiment.

As illustrated in FIG. 6, the fiber constituting the support part 16 is formed of a core material 16A. The support part 16 preferably consists of only the core material 16A. Further, when only a very slight amount of the relaxation layer 12B partially remains on the core material 16A within a range that does not affect an evaluation, such a core material 16A may also be used as needed. The core material 16 A is the same as the core material 12A in the electrode part 12. Since the support part 16 does not have a conductive layer, breakage of a conductive layer need not be considered. When the support part 16 is formed by the core material 16A, flexibility of the electronic functional member 100 is further enhanced.

Base Material

The base material 20 is not particularly limited as long as it functions as a support body for supporting the fiber net 10. The base material 20 preferably has flexibility. Here, "support" means that a part of the fiber net 10 can be fixed on a surface on one side of the base material 20. Also, as an example thereof, a case in which the fiber net 10 is held by the base material 20 by being present across the opening 20a is an exemplary example.

The material and the shape of the base material 20 can be arbitrarily selected, and a generally used film or the like can be used. For example, polyethylene terephthalate (PET), polyimide (PI), vinyl chloride (PVC), polycarbonate (PC), polyethylene naphthalate (PEN), polyether ether ketone (PEEK), or the like can be used for the base material 20. Also, a material having a property of being extendable and contractible such as fluorine-based rubber, urethane-based rubber, or silicon-based rubber can be used as the base material 20. The above-described materials may be used alone or two or more types thereof may be used. When the base material 20 has flexibility, the flexibility of the entire electronic functional member 100 is enhanced, and surface conformability is further enhanced.

Although a thickness of the base material 20 can be arbitrarily selected and differs according to types thereof, it is preferably 1 μm or more and 1000 μm or less. When the thickness of the base material 20 is 1 μm or more, a sufficient strength of the support body for suspending the fiber net 10 can be obtained. When the thickness of the base material 20 is 1000 μm or less, high flexibility can be obtained.

The base material 20 can have the opening 20a. The opening 20a may be formed in any portion of the base material 20, and its position is not particularly limited. A size of the opening 20a can be arbitrarily selected and is preferably a square of 10 μm or more and a square of 10 cm or less. When the size of the opening 20a is too small, since finer processing is required, it becomes difficult to form the electrode part 12 and the wiring part 14 on the fiber net 10. When the opening 20a is too large, it becomes difficult to support the fiber net 10 with the base material 20. The shape of the opening 20a does not have to be a quadrangular and may be circular or any other shape. In a case of a circular shape, a diameter thereof is preferably 10 μm or more and 10 cm or less.

An opening ratio of the opening 20a and the fiber net 10 can be arbitrarily selected and is preferably 10% to 99%. The fiber net 10 has a portion in which fibers are formed and a portion formed of voids. Therefore, "opening ratio of the opening 20a" means a ratio of the portion where voids are formed in a plan view of the opening 20a including the fiber net 10. The coverage of the opening and the fiber net is obtained by taking an image of a surface of the fiber net at an arbitrary 10 points in a size of 1 mm×1 mm, obtaining an area of a portion where the fibers are formed in each of the images, and obtaining an average value therefrom.

As described above, in the electronic functional member 100 according to the present embodiment, the electrode part 12 that is to be in contact with an object to be measured and the wiring part 14 that transmits measurement information are constituted by the fiber net 10. Even when an object to be measured moves, the electronic functional member 100 can conform to movement of the object to be measured due to a density of the fiber net 10 being changed and the fibers themselves constituting the fiber net 10 being extended and contracted. Therefore, the electronic functional member 100 according to the present embodiment can be used to measure an object that is very soft (Young's modulus of several kPa) and in motion such as cardiomyocytes.

Also, in the electronic functional member 100 according to the present embodiment, the fibers constituting the electrode part 12 and the wiring part 14 respectively include the relaxation layer 12B and 14B between the core materials 12A and 14A and the conductive layers 12C and 14C. The relaxation layers 12B and 14B alleviate a stress caused by a difference in a property of being extendable and contractible and flexibility respectively between the core materials 12A and 14A and the conductive layers 12C and 14C, and suppress breakage of the conductive layers 12C and 14C.

Also, in the electronic functional member 100 according to the present embodiment, the fibers constituting the electrode part 12, the wiring part 14, and the support part 16 have different configurations. When the lamination structure of the fiber is different according to a purpose required for each of the parts, the property of being extendable and contractible and the flexibility of the electronic functional member 100 can be further enhanced, and measurement for a softer material can be supported.

Method of Manufacturing Electronic Functional Member

Figure 7:
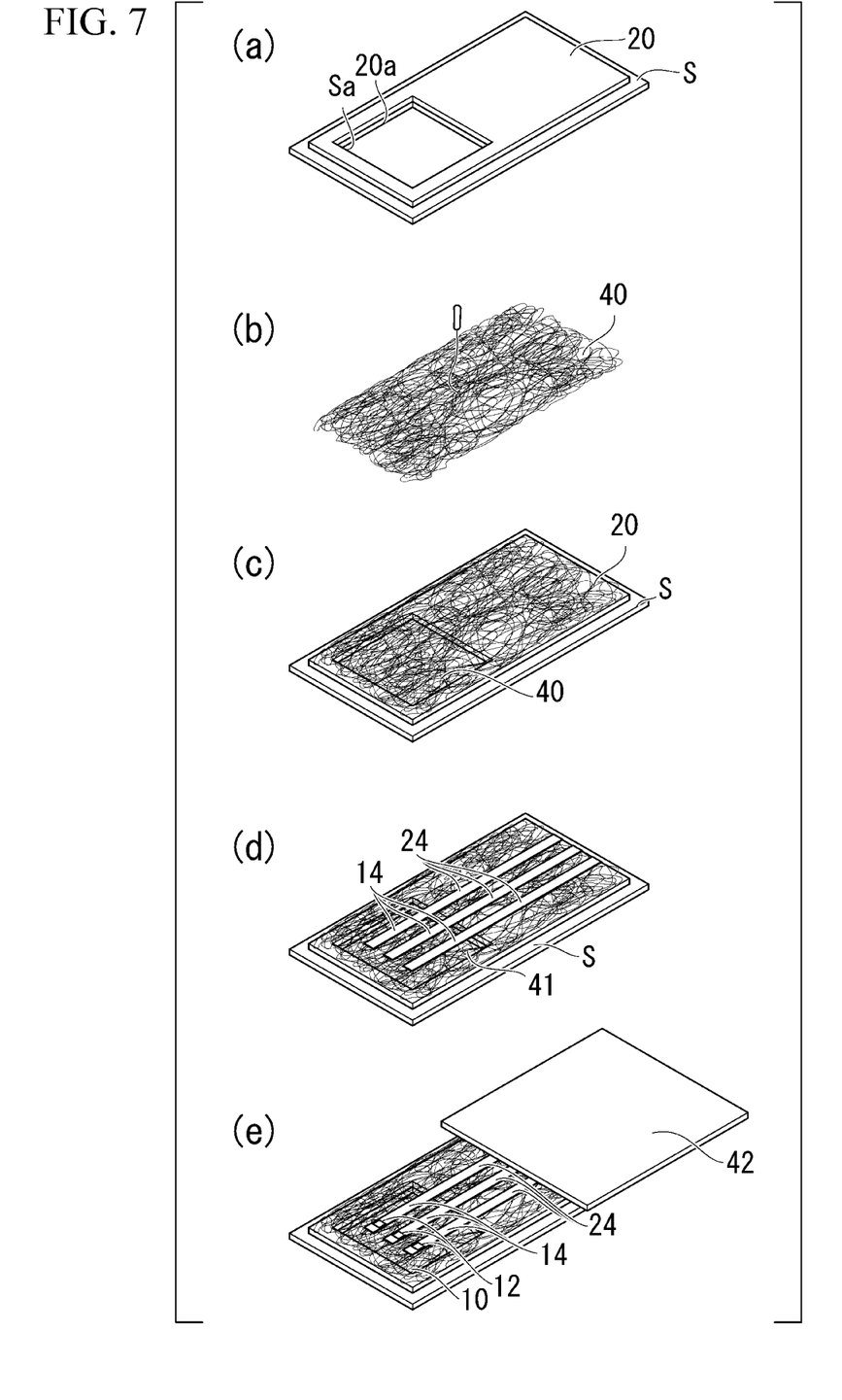
FIG. 7 is a view schematically illustrating a preferred example of a manufacturing process of the electronic functional member according to the first embodiment.

FIG. 7 is a view schematically illustrating a preferred example of a method of manufacturing an electronic functional member according to the present embodiment. The method of manufacturing the electronic functional member 100 according to the present embodiment includes a step of forming the opening 20a in the base material 20, a step of fabricating a first fiber net 40 made of a resin composition, a step of transferring and disposing the first fiber net 40 in the opening 20a of the base material 20, a step of fabricating a second fiber net 41 by laminating a relaxation layer, a conductive layer, and a cover layer in that order at a predetermined position on the first fiber net 40, and a step of fabricating the fiber net 10 by etching a part of the second fiber net 41.

First, the opening 20a is formed in the base material 20 (see (a) shown in FIG. 7). A method of forming the opening 20a in the base material 20 is not particularly limited. For example, it may be cut with a cutter or the like. In a case in which an object that is very soft (Young's modulus of several kPa) and in motion such as cardiomyocytes is measured, when a frame surrounding the opening 20a is rigid, movement of the object to be measured may be hindered. In such a case, a cut may be made at a part of the frame surrounding the opening 20a or the foregoing part may be cut off by making a cut. Also, the frame surrounding the opening 20a may be configured to be not in contact with an object to be measured.

When the opening 20a is fabricated in the base material 20, a support body S is preferably provided on a back surface of the base plate 20. When the support body S is provided, formation of the opening 20a is facilitated. Also, support body S can support the base material 20 in the step of forming a fiber net to be described below. As the support body S, glass, a resin film, or the like can be used.

When the support body S is used, an opening Sa formed in the support body S is formed on an outward side to enclose the opening 20a provided in the base material 20. This is so that fibers can be suspended on the base material 20 from a window opened in the base material in the process of transferring the fiber net in a step to be described below. When the support body S is exposed on an inward side of the opening 20a, the fiber net adheres to the support body S, and there is a likelihood of a problem such as breakage of the fiber net occurring in the process of peeling off the base material 20 from the support body S. Also, edges of the opening 20a and the opening Sa opened in the support body S may be completely coincident with each other.

Separately, a resin composition is injected using an arbitrarily selected method, preferably using an electrospinning deposition method, to fabricate the first fiber net 40 made of the resin composition (see (b) shown in FIG. 7). In the electrospinning deposition method, a solution in a syringe is pushed out while applying a high voltage between a needle of the syringe and a conductive sheet. At this time, the solution is rapidly drawn out from the syringe and sprayed toward the conductive sheet due to an electric potential difference between the needle and the conductive sheet. The sprayed solvent becomes a resin composition and forms the first fiber net 40. The first fiber net 40 is formed of the resin composition and constituted by the core material described above. Most of the solvent evaporates between the needle and a surface to be formed. An underlying base (temporary base plate) for forming the first fiber net 40 is preferably made of a material which has low adhesion to the resin composition which forms the first fiber net 40. Thereby, peeling of the first fiber net 40 after fabrication is facilitated.

Next, the fabricated first fiber net 40 is transferred to be disposed in the opening 20a of the base material 20 (see (c) shown in FIG. 7). For example, when the first fiber net 40 is fabricated on the temporary base plate that is easily peeled off as described above, the first fiber net 40 is peeled off from the temporary base plate and transferred to the opening 20a of the base plate 20. The first fiber net 40 and the base plate 20 are brought into close contact with each other only by pressing the first fiber net 40 against an edge portion of the base plate 20. Also, the transfer step is not limited to the above-described method, and other methods such as, for example, the following method may be used. The first fiber net 40 is formed with respect to a large ring-shaped conductive member using an electrospinning method such that the first fiber net 40 is suspended by the ring. The base material 20 having the opening 20a is caused to pass from one side of the ring toward the other side. Then, the base material 20 is in a state of being entangled with the formed first fiber net 40. Thereby, the formed first fiber net 40 is transferred to the opening 20a, and thereby the first fiber net 40 is formed in the opening 20a.

Further, the method of fabricating the first fiber net 40 is not limited to the electrospinning method. A sheet made of a fine fiber may be fabricated, cut thereafter, and then laminated on the base material 20 such that the opening part 20a is covered by the sheet. At this time, the sheet made of the fine fiber is a non-woven fabric having voids. Also, when the material of the fibers is a thermoplastic polymer, the sheet can be easily laminated using thermo-compression bonding.

Figure 8:
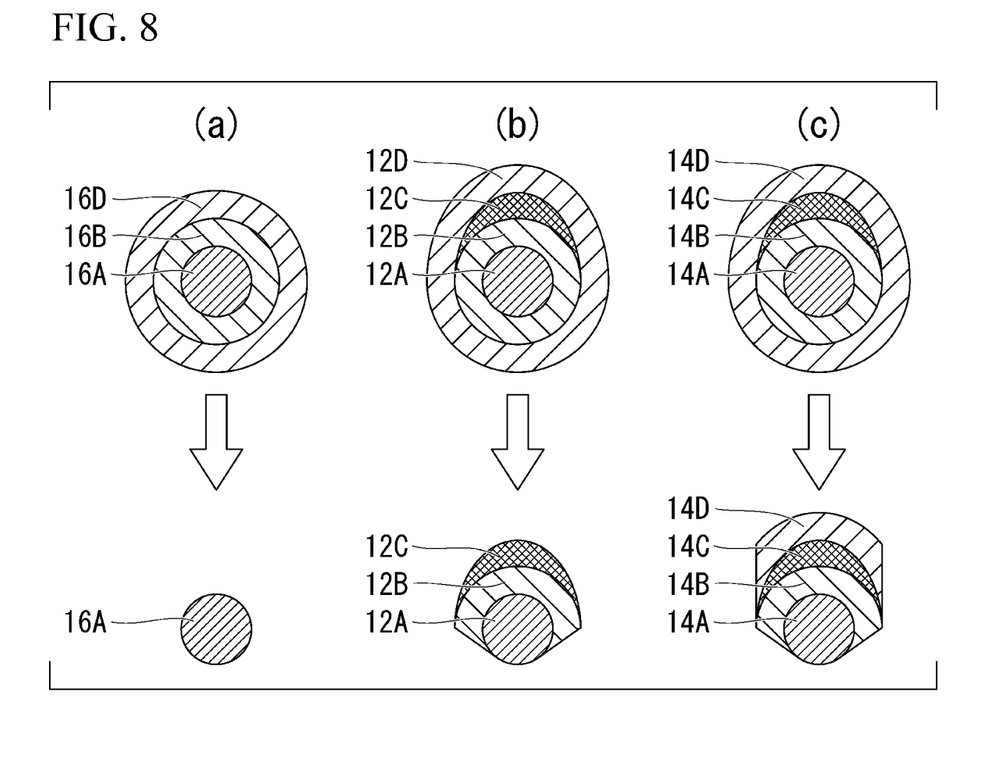
FIG. 8 is a view schematically illustrating a state in a manufacturing process of each fiber constituting the fiber net of the electronic functional member according to the first embodiment.

Next, the second fiber net 41 is fabricated by laminating a relaxation layer, a conductive layer, and a cover layer in that order at a predetermined position of the first fiber net 40. A fiber constituting the fiber net includes a plurality of types (3 or 4 types in the present example) according to the role. A preparation process of each of the types will be described with reference to FIG. 8. FIG. 8 is a view schematically illustrating a state in a manufacturing process of each fiber constituting the fiber net of the electronic functional member according to the present embodiment.

The first fiber net 40 is an aggregate of fibers. A core material of the fiber constituting the first fiber net 40 is illustrated as the core material 16A located at a position, which corresponds to the fabricated support part 16 (see (a) shown in FIG. 8), illustrated as the core material 12A located at a position, which corresponds to the fabricated electrode part 12 (see (b) shown in FIG. 8), and illustrated as the core material 14A located at a position, which corresponds to the fabricated wiring part 14 (see (c) shown in FIG. 8). Further, although different numbers 12, 14, and 16 are used to facilitate reference, when alphabets added to these numbers are the same, it means that the same material may be used.

First, a relaxation layer is laminated on the entire first fiber net 40. As a result, the core material 16A is covered with a relaxation layer 16B at the position, which corresponds to the fabricated support part 16 (see (a) shown in FIG. 8). The core material 12A is covered with the relaxation layer 12B at the position, which corresponds to the fabricated electrode part 12 (see (b) shown in FIG. 8). The core material 14A is covered with the relaxation layer 14B at the position, which corresponds to the fabricated wiring part 14 (see (c) shown in FIG. 8). As a laminating method, an arbitrarily selected method can be used, and for example, a sputtering method, a chemical vapor deposition (CVD) method, or the like can be used. In order to enhance coverage of the relaxation layer, a CVD method which has excellent coverage performance is preferably used.

Next, a conductive layer is laminated at positions which corresponds to the electrode parts 12 and the wiring parts 14 of the first fiber net 40.

A shape of the conductive layer can be arbitrarily changed by a method that can be selected as needed, for example, by performing patterning. As a method of patterning, layer-formation through a mask is most convenient and preferable. When the patterning is performed, the conductive layer is not laminated at the position, which corresponds to the fabricated support part 16 (see (a) shown in FIG. 8). On the other hand, the core material 12A, the relaxation layer 12B, and the conductive layer 12C are laminated in that order at the position, which corresponds to the fabricated electrode part 12 (see (b) shown in FIG. 8). The core material 14A, the relaxation layer 14B, and the conductive layer 14C are laminated in that order at the position, which corresponds to the fabricated wiring part 14 (see (c) shown in FIG. 8). An opening shape of the mask can be selected as needed. For example, a mask having an opening at positions, which corresponds to the electrode part 12 and the wiring part 14 can be used.

Further, the second fiber net 41 having a cover layer is formed (see (d) shown in FIG. 7) by laminating the cover layer on the entire first fiber net 40 processed as described above. As a result, the core material 16A, the relaxation layer 16B, and the cover layer 16D are laminated in that order at the position, which corresponds to the fabricated support part 16 (see (a) shown in FIG. 8). The core material 12A, the relaxation layer 12B, the conductive layer 12C, and the cover layer 12D are laminated in that order at the position, which corresponds to the fabricated electrode part 12 (see (b) shown in FIG. 8). The core material 14A, the relaxation layer 14B, the conductive layer 14C, and the cover layer 14D are laminated in that order at the position, which corresponds to the fabricated wiring part 14 (see (c) shown in FIG. 8). A method of laminating the cover layer can be arbitrarily selected, and for example, a sputtering method, a chemical vapor deposition (CVD) method, or the like can be used.

Finally, the fiber net 10 is fabricated by etching a part of the fabricated second fiber net 41 (see (e) shown in FIG. 7). A preferred example of etching will be described below.

A predetermined position of the second fiber net 41 is masked at first, for example, one surface at the position which corresponds to the wiring part 14 is masked. Then, etching processing is performed. Only the wiring part 14 is not etched. Dry etching is preferably used for the etching. In the case of dry etching, one surface of the fiber net may be etched, and then a surface on the opposite side may be etched. Further, a mask may or may not be used on the surface of the opposite side.

In the present etching step, the number of times of etching, a surface (upper surface, lower surface, or both) on which etching is implemented, the strength of etching, a combination of etching and a mask, and presence or absence of a mask can be arbitrarily selected. As the mask, two or more masks having different openings may be used as needed. For example, a mask having an opening at positions corresponding to the support part 16 and the electrode part 12, a mask having an opening at a position corresponding to the support part 16, a mask having an opening at a position corresponding to the wiring part 14, and a mask having an opening at a position corresponding to the electrode part 12 can be used. A mask without an opening may be used to cover a portion of the fiber net. These masks may be used alone or in combination as needed.

A configuration as described below can be obtained after a surface on the opposite side is also etched, for example, after the opposite side is etched without a mask.

At the position which corresponds to the support part 16 after fabrication, the relaxation layer 16B and the cover layer 16D are removed by etching, and only the core material 16A remains (see below the arrow in (a) shown in FIG. 8).

At the position which corresponds to the electrode part 12 after fabrication, the cover layer 12D on one surface side (an upper side in FIG. 8) and the cover layer 12D and the relaxation layer 12B on the other surface side (a lower side in FIG. 8) are removed by etching (see below the arrow in (b) shown in FIG. 8). That is, the conductive layer 12C is exposed on one surface side, and the electrode part 12 functions as an electrode (see below the arrow in (e) shown in FIG. 7).

At the position which corresponds to the wiring part 14 after fabrication, one surface side (upper side in FIG. 8) has not been etched since the surface side was masked, and the other surface side has been etched to remove the cover layer 14D and the relaxation layer 14B (see (c) shown in FIG. 8). As described above, the conductive layer 14C is not exposed in the wiring part 14.

With the procedure described above, the fiber net 10 in which structures of the fibers constituting the electrode part 12, the wiring part 14, and the support part 16 are different can be fabricated. The support body S can be detached after the fiber net 10 is formed. Also, when an external terminal, for example, an external terminal 42 including a plurality of electrodes is connected to a second end portion of the wiring part 14 on a side opposite to a first end portion to which the electrode part 12 is provided, connection to the outside is possible (see (e) shown in FIG. 7). The plurality of electrodes of the external terminal 42 can be respectively connected to the conductive layers 14C exposed at the second end portions of a plurality of wiring parts 14.

Electronic Component

An electronic component according to a second embodiment includes an electronic circuit element connected to the wiring part of the electronic functional member described above.

Figure 9:
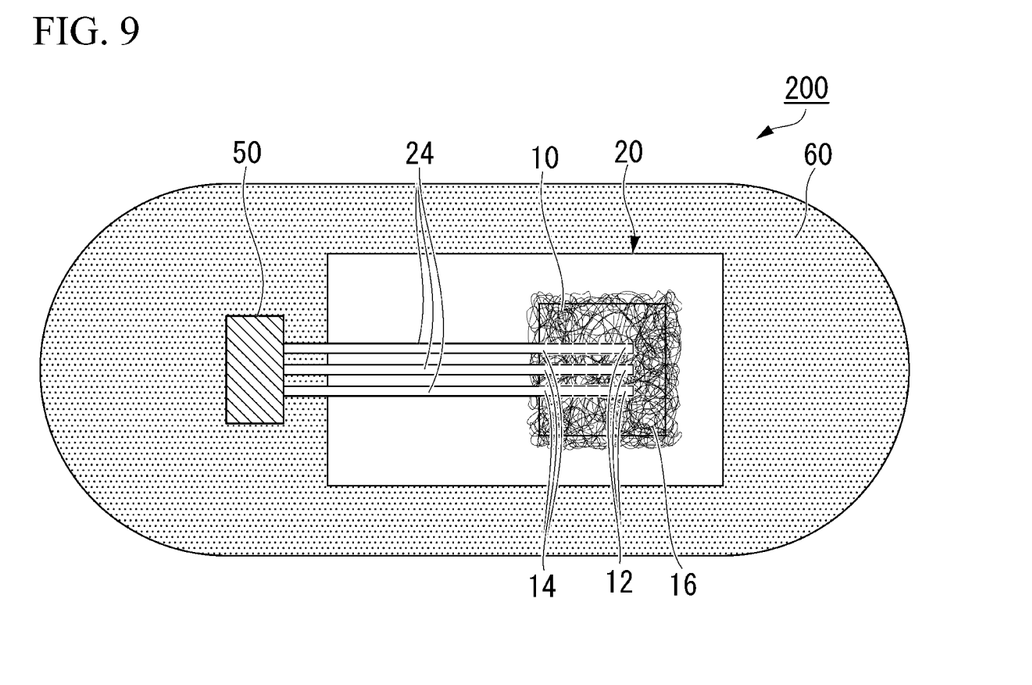
FIG. 9 is a schematic view schematically illustrating a preferred example of an electronic component according to a second embodiment.

FIG. 9 is a view schematically illustrating an example of an electronic component according to the present embodiment. An electronic component 200 according to the present embodiment includes the electronic functional member 100, an integrated circuit 50 joined by the wiring parts 14 and 24 of the electronic functional member 100, and a cover film 60 formed to cover the electronic functional member 100 and the integrated circuit 50.

The electronic functional member 100 is used to measure information of a surface to be measured with the electrode part 12 of the electronic functional member 100. The measured information is transmitted to the integrated circuit 50 via the wiring parts 14 and 24. The integrated circuit 50 transmits the obtained information to a receiver (not illustrated) wirelessly or the like. Information is output to the outside by such a procedure.

The electronic component 200 illustrated in FIG. 9 includes the cover film 60 that covers the electronic functional member 100 and the integrated circuit 50. The cover film 60 can enhance adhesion to an object to be measured. The cover film 60 may not be provided depending on a usage mode.

The integrated circuit 50 is not particularly limited. Generally used one can be used as long as information can be transmitted to the outside. As the cover film 60, one generally used for a sticking plaster or the like can be used.

EXAMPLES

Example 1

A film made of parylene was used as a base material, and an opening of 1 cm×2 cm was formed therein.

At this time, a polyimide film in which an opening of the same size was formed was used as a support body on a back surface of the parylene.

On the other hand, a first resin net made of polyurethane was fabricated on a temporary base plate using an electrospinning method. A diameter of the fiber (polyurethane) constituting the first resin net was 700 nm to 800 nm, and there was some variation. The first resin net fabricated on the temporary base plate was peeled off from the temporary base plate and transferred to cover the opening of the base material.

Next, the first resin net was covered with 200 nm of parylene as a relaxation layer. Accordingly, a core material was covered with the relaxation layer. Nest, vapor deposition via a mask was performed to provide Au as a conductive layer at a predetermined position of the first resin net. Then, the first resin net that had been processed using the aforementioned vapor deposition is laminated again by 200 nm of parylene as a cover layer to generate a second fiber net.

Finally, unnecessary portions of the cover layer and the relaxation layer were removed using a dry etching method to fabricate the fiber net. With respect to the electrode part, the wiring part and the support part, the fiber structure of the fiber net was formed according to the structure shown in FIG. 8.

The fiber net fabricated in example 1 was pulled in one direction and elongated by 12%. Extension and contraction of the fiber net fabricated in example 1 were repeated 500 times, and then resistance between the electrode part and an end portion of the wiring part (end portion on a side opposite to the electrode part) in the fiber net was measured. As a result, there was no change in a resistance value between a resistance value measured immediately after the fabrication and a resistance value measured after the processing of extension and contraction.

That is, in the fiber net fabricated in example 1, breakage of the conductive layer was curbed by forming the relaxation layer in the electrode part and the wiring part.

The fiber net fabricated in example 1 was able to withstand extension and contraction in which a shape thereof changed by 30%. Therefore, the fiber net can be used to measure an object that is very soft (Young's modulus of several kPa) and in motion such as, for example, cardiomyocytes. In practice, an electric potential measurement could be performed without hindering movement of cardiomyocytes using the fiber net fabricated in example 1.

INDUSTRIAL APPLICABILITY

According to the present invention, it is possible to provide an electronic functional member and an electronic component capable of preventing a conductive layer from being damaged at the time of being extended and contracted.

REFERENCE SIGNS LIST

10 Fiber net
12 Electrode part 14, 24 Wiring part
16 Support part
12A, 14A, 16A. 32A Core material
12B, 14B, 16B Relaxation layer
12C, 14C, 32C Conductive layer
12D, 14D, 16D Cover layer
20 Base material
S Support body
20a, Sa Opening
40 First fiber net
41 Second fiber net
42 External terminal
50 Integrated circuit
60 Cover film
100 Electronic functional member
200 Electronic component

What is claimed is:

1. An electronic functional member comprising:
a fiber net which includes an electrode part,
wherein
a fiber which constitutes the electrode part includes:
a core material;
a relaxation layer which covers at least a part of a surface of the core material and contains a material which has a higher Young's modulus than a material which forms the core material; and
a conductive layer which covers a surface of the relaxation layer on a side opposite to the core material side.

2. The electronic functional member according to claim 1, wherein a Young's modulus of the material which forms the core material is lower than 1 GPa, and a Young's modulus of a material which forms the relaxation layer is 1 GPa or higher.

3. The electronic functional member according to claim 1, wherein
the material which forms the core material is polyurethane or silicone rubber, and
a material which forms the relaxation layer is parylene.

4. The electronic functional member according to claim 1, wherein the conductive layer is made of gold or platinum.

5. The electronic functional member according to claim 1, wherein
a diameter of the core material is 200 nm or more and 2000 nm or less, and
a thickness of the relaxation layer is 50 nm or more and 500 nm or less.

6. The electronic functional member according to claim 1, further comprising a wiring part which continuously extends from the electrode part, wherein
a fiber which constitutes the wiring part includes:
the core material;
the relaxation layer;
the conductive layer; and
a cover layer which covers a surface of the conductive layer on a side opposite to the relaxation layer side.

7. The electronic functional member according to claim 6, wherein
a fiber which constitutes a portion of the fiber net excluding the electrode part and the wiring part is formed of a core material, and
the core material, the core material of the electrode part, and the core material of the wiring part are formed of the same material.

8. An electronic component comprising:
the electronic functional member according to claim 7; and
an electronic circuit element connected to the wiring part of the electronic functional member.

9. The electronic functional member according to claim 1, wherein
the conductive layer is in contact with the relaxation layer, and
the relaxation layer is in contact with the core material.

10. The electronic functional member according to claim 1, wherein a Young's modulus of a material which forms the relaxation layer is higher than a Young's modulus of the material which forms the core material and lower than a Young's modulus of a material which forms the conductive layer.

11. The electronic functional member according to claim 1, wherein the relaxation layer covers an entire surface of the core material.

12. The electronic functional member according to claim 1, wherein the relaxation layer covers a part of the surface of the core material.

13. The electronic functional member according to claim 1, wherein the core material and the conductive layer are not in contact with each other.

14. The electronic functional member according to claim 1, wherein a surface of the conductive layer is exposed in air.

15. The electronic functional member according to claim 1, wherein the fiber included in the electrode part is a plurality of fibers, and the fibers are in contact with each other.

* * * * *